United States Patent [19]

Pujado

[11] 4,370,205

[45] Jan. 25, 1983

[54] RECOVERY OF CUMENE FROM A MIXTURE THEREOF WITH PHENOL AND WATER

[75] Inventor: Peter R. Pujado, Palatine, Ill.

[73] Assignee: UOP Inc., Des Plaines, Ill.

[21] Appl. No.: 289,592

[22] Filed: Aug. 3, 1981

[51] Int. Cl.³ .............. B01D 3/14; C07C 37/74; C07C 7/04
[52] U.S. Cl. .................... 203/75; 203/77; 568/754; 585/804
[58] Field of Search .......... 585/804; 568/754; 203/74, 75, 77, 81, 82, 14

[56] References Cited

U.S. PATENT DOCUMENTS

| | | | |
|---|---|---|---|
| 2,757,209 | 7/1956 | Joris | 568/754 |
| 3,151,047 | 9/1964 | Moon et al. | 203/75 |
| 3,365,375 | 1/1968 | Nixon | 203/82 |
| 3,405,038 | 10/1968 | Kohmoto | 203/81 |
| 3,441,618 | 4/1969 | Flickinger | 568/754 |
| 4,166,772 | 9/1979 | Murtha | 568/754 |
| 4,262,150 | 4/1981 | Pujado | 568/754 |
| 4,262,151 | 4/1981 | Pujado | 568/754 |

*Primary Examiner*—Wilbur L. Bascomb, Jr.
*Attorney, Agent, or Firm*—James R. Hoatson, Jr.; Robert W. Welch; William H. Page, II

[57] ABSTRACT

A process is disclosed for the recovery of a phenol-free cumene fraction from a mixture thereof with phenol and water. Said mixture is introduced into a first fractionation column at conditions to separate a bottom fraction comprising a major portion of said phenol and an overhead fraction comprising said cumene and water and a residual portion of said phenol. The overhead fraction is condensed to form an aqueous phase containing a minor portion of the residual phenol and a water-saturated organic phase comprising cumene and the balance of said residual phenol. The water-saturated organic phase is then further treated in a second fractionation column whereby cumene is recovered as an overhead fraction substantially free of phenol.

7 Claims, 1 Drawing Figure

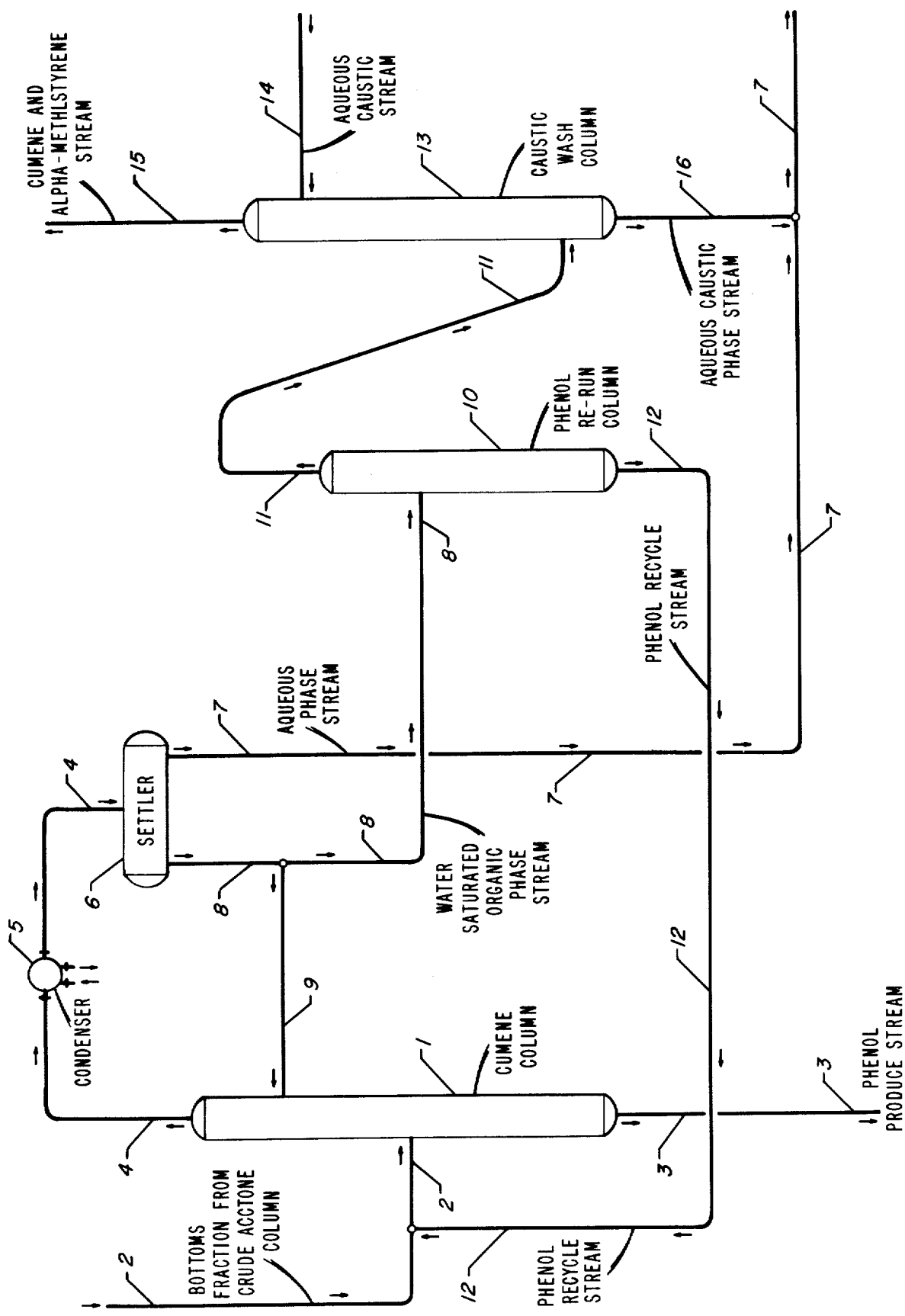

RECOVERY OF CUMENE FROM A MIXTURE THEREOF WITH PHENOL AND WATER

This invention relates to the manufacture of phenols by the acid cleavage of an alpha-hydroperoxy derivative of an alkyl-substituted aromatic hydrocarbon. In particular, this invention relates to the manufacture of phenol by the acid cleavage of cumene hydroperoxide.

In general, phenols are prepared by the oxidation of an alkyl-substituted aromatic hydrocarbon, preferably a secondary alkyl-substituted aromatic hydrocarbon, followed by the acid cleavage of the resulting alpha-hydroperoxy derivative thereof. The acid cleavage is typically effected by means of an aqueous acid, usually a 50–98% aqueous sulfuric acid solution, although at least a 70% solution is preferred. Other suitable aqueous acids include aqueous hydrochloric or perchloric acid solutions. The acid cleavage reaction mixture will include a phenol, a ketone, water and unreacted alkyl-substituted aromatic hydrocarbon. The present invention is particularly directed to a process wherein phenol is prepared by the air oxidation of cumene, and by the subsequent sulfuric acid cleavage of the resulting cumene hydroperoxide. In addition to the principal products of phenol and acetone, the acid cleavage reaction mixture will further contain varying amounts of by-products, principally alpha-methylstyrene, as well as unreacted cumene.

In the process of recovering phenol from the acid cleavage reaction mixture, the reaction mixture is initially neutralized, either directly by the addition of caustic or indirectly by contact with an ion-exchange resin. In any case, the neutralized reaction mixture is fed to a distillation column, commonly referred to as a crude acetone column, at conditions to effect a crude separation of those materials boiling below phenol whereby an overhead fraction is recovered comprising substantially all of the acetone and lower boiling by-products as well as a substantial portion of the water and unreacted cumene. Acetone is subsequently recovered by further distillation of the crude acetone column overhead, the cumene being recycled to the crude acetone column.

The bottoms fraction recovered from the crude acetone column, comprising phenol, cumene, alpha-methylstyrene and water, is fed to a distillation column commonly referred to as a cumene or alpha-methylstyrene column. The bottoms fraction from the crude acetone column is typically treated for the separation of heavy ends prior to distillation in the cumene column, although said treatment may be subsequent thereto. In any case, the cumene column is operated at conditions to separate an overhead fraction comprising water, cumene and alpha-methylstyrene from the higher boiling phenol product. The phenol, recovered as the bottoms fraction, further contains certain impurities, e.g., mesityl oxide, hydroxy acetone, and the like, and said impurities are separated from the phenol product on further distillation.

The overhead fraction recovered from the cumene column will invariably comprise an azeotropic mixture of phenol and water admixed with the alpha-methylstyrene and unreacted cumene. While the alpha-methylstyrene can be separated and recovered as a useful by-product, it is more frequently subjected to hydrogenation and reduced to cumene in admixture with the unreacted cumene for recycle to the aforementioned oxidation step of the process. A significant amount of phenol is present in the overhead fraction from the cumene column, including phenol in azeotropic mixture with water and difficult to remove by simple distillation. A small portion of this phenol is rejected with the water phase separated upon condensation of the heterogeneous azeotrope. However, the organic phase consisting mostly of cumene and alpha-methylstyrene will be contaminated with phenol as corresponds to the partition coefficient of phenol between the aqueous phase and the organic phase. Since phenol is well known as a powerful oxidation inhibitor, substantially all of the phenol must be separated from the cumene prior to recycle to the oxidation phase of the process. This has heretofore been accomplished by subjecting the overhead fraction from the cumene column to a caustic wash involving a considerable volume of caustic.

It is an object of this invention to present an improved method for the separation of cumene from a mixture thereof with phenol whereby the cumene is recovered substantially reduced in phenol and requiring minimal caustic wash.

In one of its broad aspects, the present invention embodies a process for the recovery of a secondary alkylbenzene from a mixture thereof with water and a phenol derivative of said secondary alkylbenzene which comprises the steps of (a) introducing said mixture into a first fractionation column and separating a bottoms fraction comprising a major portion of said phenol, and an overhead fraction comprising said secondary alkylbenzene, water, and the residual portion of said phenol; (b) discharging said bottoms fraction; (c) condensing said overhead fraction and separating an aqueous phase containing a minor portion of said residual phenol, and a water-saturated organic phase comprising said secondary alkylbenzene and the balance of said residual phenol; (d) discharging said aqueous phase; (e) introducing the water-saturated organic phase into a second fractionation column, separating a phenol bottoms fraction, and recovering a secondary alkylbenzene overhead fraction having a reduced phenol concentration substantially equivalent to that in azeotropic mixture with said saturation water.

One of the more specific embodiments concerns a process for the recovery of cumene from a mixture thereof with phenol and water which comprises the steps of (a) introducing said mixture into a first fractionation column operated at a bottom temperature of from about 160° to about 180° C. and a bottom pressure of from about 600 to about 760 mm Hg, and at a top temperature of from about 90° to about 105° C. and a top pressure of from about 100 to about 150 mm Hg and separating a bottoms fraction comprising the major portion of said phenol, and an overhead fraction comprising cumene, water, and the residual portion of said phenol; (b) discharging said bottoms fraction; (c) condensing said overhead fraction at a temperature of from about 40° to about 50° C. and a pressure of from about 75 to about 125 mm Hg, to separate an aqueous phase containing a minor portion of said residual phenol, and a water-saturated organic phase comprising cumene and the balance of said residual phenol; (d) discharging said aqueous phase; (e) introducing the water-saturated organic phase into a second fractionation column operated at a bottom temperature of from about 160° to about 180° C. and a bottom pressure of from about 600 to about 760 mm Hg, and at a top temperature of from about 90° to about 105° C. and a top pressure of from about 100 to about 150 mm Hg, separating a phenol bottoms fraction and recovering a cumene overhead fraction having a reduced phenol concentration substantially equivalent to that in azeotropic mixture with said saturation water.

Other objects and embodiments of this invention will become apparent in the following detailed specification.

The overall process to which this invention pertains concerns the oxidation of a secondary alkylbenzene, for example, isopropylbenzene (cumene), isobutylbenzene, isoamylbenzene, 1-methyl-4-isopropylbenzene, p-diisopropylbenzene, p-diisobutylbenzene, 1-isopropyl-4-isobutylbenzene, cyclohexylbenzene, and the like, to form the corresponding hydroperoxide, i.e., isopropylbenzene hydroperoxide, isobutylbenzene hydroperoxide, isoamylbenzene hydroperoxide, 1-methyl-4-isopropylbenzene hydroperoxide, p-diisopropylbenzene hydroperoxide, p-diisobutylbenzene hydroperoxide, 1-isobutyl-4-isopropylbenzene hydroperoxide, cyclohexylbenzene hydroperoxide, and the like. The present invention is particularly directed to the recovery of unreacted cumene from a reaction mixture resulting from the acid cleavage of cumene hydroperoxide, said cumene being recovered substantially free of phenol for recycle to the oxidation phase of the overall phenol manufacturing process.

The aforesaid oxidation reaction is effected at conditions well known in the art. The hydroperoxide oxidation product can be prepared by direct liquid phase oxidation of the selected alkylbenzene with oxygen, or an oxygen-containing gas such as air, usually at an elevated temperature. The oxidation reaction proceeds slowly through an initial induction period, accelerating to a more favorable rate with the formation of the hydroperoxide which exerts a catalytic effect on the oxidation reaction. This initial induction period is eliminated, or substantially reduced, by initially including a hydroperoxide in the reaction mixture, usually the hydroperoxide product of the reaction. However, other materials are disclosed in the art which exhibit a similar catalytic effect. Temperatures effecting the oxidation reaction range from about room temperature to about the boiling point of the hydrocarbon subjected to oxidation, which, in the case of cumene, is about 305° F. In general, it is preferred to utilize an elevated temperature in the range of from about 120° to about 265° F. The optimum temperature will depend on the particular alkylbenzene to be oxidized and on the reaction conditions otherwise employed. The oxidation can be effected at pressures ranging from about atmospheric to about 500 psig, although a pressure not exceeding about 90 psig is generally preferred. It is desirable to limit the contact time of the reactants at oxidation conditions to effect substantially less than complete conversion of the alkylbenzene to the corresponding hydroperoxide. For example, in the oxidation of cumene, it is desirable to limit the contact time of the cumene and the oxidizing agent so that the concentration of the resulting cumene hydroperoxide does not exceed about 30 wt. %.

The further description of the process of this invention is presented with reference to the attached drawing. The drawing is a simplified flow diagram representing one preferred embodiment of this invention and is not intended as an undue limitation on the generally broad scope of the invention as set out in the appended claims. Certain hardware such as valves, pumps, compressors, heat exchangers, instrumentation and controls, have been omitted as not essential to a clear understanding of the invention, the use and application of said hardware being well within the skill of the art.

Referring then to the drawing, there is shown a cumene column 1, a settler 6, a phenol re-run column 10 and a caustic wash column 13. A bottoms fraction from a crude acetone column, which is not shown, is introduced into the cumene column 1 through line 2. A bottoms fraction from a crude acetone column will typically comprise about 128.7 moles of phenol, 28.7 moles of cumene, 4.8 moles of alpha-methylstyrene, 38.4 moles of water and about 0.3 mole of acetone on an hourly basis, and also a small amount of higher boiling materials. These higher boiling materials may either be separated before the cumene column or after the cumene column. This stream, passing through line 2, is admixed with a recycle stream from line 12 comprising about 3.2 moles of phenol per hour, said recycle stream originating as hereinafter described. The combined streams are then continued through line 2 into the cumene column 1. The cumene column 1 is operated at a bottom temperature of from about 160° to about 180° C. and a bottom pressure of from about 600 to about 760 mm Hg pressure. The cumene column is further operated at a top temperature of from about 90° to about 105° C. and at a top pressure of from about 100 to about 150 mm Hg whereby an overhead fraction is recovered through line 4 comprising about 28.6 moles of cumene and 4.5 moles of alpha-methylstyrene per hour as well as about 3.4 moles of phenol, 0.3 mole of acetone and 38.4 moles of water. A phenol product stream is withdrawn from the bottom of a cumene column 1 via line 3, and said phenol product stream comprises about 128.5 moles of phenol, 0.1 mole of cumene, and 0.3 mole of alpha-methylstyrene on an hourly basis. This crude phenol stream, also containing a trace of water and the aforementioned higher boiling materials, is continued through line 3 and further treated in conventional distillation means, not shown, for the recovery of a substantially pure phenol product.

The overhead fraction recovered through line 4 is passed through a condensing means 5 situated in line 4, and the resulting condensate is collected in a settler 6 operated at a temperature of from about 40° to about 50° C. and at a pressure of from about 75 to about 125 mm Hg whereby an aqueous phase settles out, and a water-saturated organic phase separates as an upper liquid layer. The lower aqueous phase is recovered and discharged through line 7. The aqueous phase thus recovered comprises about 38.3 moles of water, 0.2 mole of phenol and 0.1 mole of acetone on an hourly basis, and also a trace of cumene and alpha-methylstyrene. The water-saturated organic phase is withdrawn from the settler 6 by way of line 8, and one portion is diverted to the top of the cumene column 1 via line 9 to maintain a reflux ratio therein of about 1.8. The balance of the organic phase is continued through line 8 and introduced into a phenol re-run column 10 operated at substantially the same conditions as employed in the cumene column 1. The organic phase introduced into the re-run column comprises about 28.6 moles of cumene and 4.5 moles of alpha-methylstyrene per hour as well as about 3.2 moles of phenol, 0.2 mole of acetone and about 0.1 mole of saturation water. In the re-run column 10, substantially all of the phenol, about 3.2 moles per hour, is separated as a bottoms fraction via line 12, and this phenol is recycled to the cumene column 1 by way of line 12 and line 2 as heretofore mentioned. The overhead fraction from the re-run column, comprising about 28.6 moles of cumene and 4.5 moles of alpha-methylstyrene per hour, and also a trace of phenol substantially equivalent to that in azeotropic mixture with the aforesaid saturation water, is withdrawn through line 11 and transferred to the bottom of a caustic wash column 13. An aqueous caustic stream charged to the upper portion of the caustic wash column by way of line 14 provides about 0.01 mole of sodium hydroxide and 0.14 mole of water thereto per hour. The cumene/alpha-methylstyrene organic phase passes upwardly in countercurrent contact with the aqueous caustic phase and in the process phenol is recovered in the caustic as sodium phenate. The aqueous caustic phase is recovered from the caustic wash column 13 through line 16, combined with the aqueous phase passing through line 7, and further treated for the recovery of phenol by conventional means which are not shown. In practice, a closed loop of aqueous phase containing both caustic and sodium phenate may be maintained around the caustic wash column 13 so as to achieve a sufficiently high contacting efficiency, e.g., sufficient hole velocity if sieve trays are used as contacting devices in the caustic wash column. Should this be the case, stream lines 14 and 16 should be regarded as net caustic make-up and sodium phenate withdrawal lines, respectively. An excess of caustic would normally be fed through line 14 and withdrawn through line 16 in the present configuration. In any case, essentially all of the cumene and alpha-methylstyrene, now typically containing less than 30 ppm phenol by weight, is recovered from the caustic wash column 13 through an overhead line 15 at a rate of about 28.6 moles of cumene and 4.5 moles of alpha-methylstyrene per hour. This stream is typically hydrotreated to convert the alpha-methylstyrene portion thereof to cumene, and the hydrotreated stream is then recycled to the oxidation phase of the overall process. Alternatively, the alpha-methylstyrene can be recovered as a useful by-product by conventional distillation means and the remaining cumene recycled to the oxidation reactor.

As heretofore mentioned, phenol is a well-known and powerful oxidation inhibitor substantially all of which must be separated from the cumene prior to recycle to the oxidation phase of the phenol manufacturing process. The separation is typically by means of a caustic wash requiring a substantial volume of caustic. The process of the present invention allows a substantial reduction in the volume of caustic, and a consequent reduction in the volume of waste water which must be treated prior to disposal.

I claim as my invention:

1. A process for the recovery of a secondary alkylbenzene from a mixture thereof with water and a phenol derivative of said secondary alkylbenzene which comprises the steps of:
   (a) introducing said mixture into a first fractionation column and separating a bottoms fraction comprising the major portion of said phenol derivative, and an overhead fraction comprising said secondary alkylbenzene, water and the residual portion of said phenol derivative;
   (b) discharging said bottoms fraction;
   (c) condensing said overhead fraction and separating an aqueous phase containing a minor portion of said residual phenol derivative, and a water-saturated organic phase comprising said secondary alkylbenzene and the balance of said residual phenol derivative;
   (d) discharging said aqueous phase; and,
   (e) introducing the water-saturated organic phase into a second fractionation column, separating a phenol derivative bottoms fraction, and recovering a secondary alkylbenzene overhead fraction having a reduced phenol derivative concentration substantially equivalent to that in azeotropic mixture with said saturation water.

2. The process of claim 1 further characterized in that said secondary alkylbenzene is cumene and said phenol derivative of said secondary alkylbenzene is phenol.

3. The process of claim 2 further characterized in that at least a portion of the water-saturated organic phase of step (c) is recycled to the top of said first fractionation column to maintain an external reflux to feed ratio therein of from about 1.5 to about 2.

4. The process of claim 2 further characterized in that the phenol bottoms fraction separated in accordance with step (e) is recycled to said first fractionation column.

5. The process of claim 2 further characterized in that said first fractionation column is operated at a bottom temperature of from about 160° to about 180° C. and a bottom pressure of from about 600 to about 760 mm Hg., and a top temperature of from about 90° to about 105° C. and a top pressure of from about 100 to about 150 mm Hg.

6. The process of claim 2 further characterized with respect to step (c) in that said overhead fraction is condensed at a temperature of from about 40° to about 50° C. and at a pressure of from about 75 to about 125 mm Hg.

7. The process of claim 2 further characterized with respect to step (e) in that said second fractionation column is operated at a bottom temperature of from about 160° to about 180° C. and a bottom pressure of from about 600 to about 760 mm Hg, and at a top temperature of from about 90° to about 105° C. and a top pressure of from about 100 to about 150 mm Hg.

* * * * *